United States Patent [19]

Allievi

[11] 4,012,467
[45] Mar. 15, 1977

[54] PROCESS FOR PREPARING AN ESTER OF THE N-METHYL-N-HYDROXYETHYLGUANI-DINE

[76] Inventor: Elio Allievi, Via G. Macchi, 6, Cantu'(Como), Italy

[22] Filed: Oct. 30, 1975

[21] Appl. No.: 627,378

[30] Foreign Application Priority Data

Nov. 13, 1974 Italy .................................. 29373/74

[52] U.S. Cl. ................................ 260/978; 260/945
[51] Int. Cl.$^2$ .......................................... C07F 9/08
[58] Field of Search .......... 260/944, 945, 978, 980; 424/211

[56] References Cited

UNITED STATES PATENTS 3,692,881  9/1972  Stanford et al. ............... 260/945 X

OTHER PUBLICATIONS

Ferrari et al., Chemical Abstracts, vol. 74 (1971) 79645y.
Rapuzzi et al., Chemical Abstracts, vol. 74 (1971) 96598c.

Primary Examiner—Richard L. Raymond
Attorney, Agent, or Firm—Stevens, Davis, Miller & Mosher

[57] ABSTRACT

Process for preparing the phosphoric ester of N-methyl-N-hydroxyethylguanidine by reacting the phosphate of N-methyl-N-hydroxyethylguanidine with polyphosphoric acid.

4 Claims, No Drawings

PROCESS FOR PREPARING AN ESTER OF THE N-METHYL-N-HYDROXYETHYLGUANIDINE

The present invention refers to a new process for preparing the phosphoric ester of N-methyl-N-hydroxyethylguanidine.

The phosphoric ester of N-methyl-N-hydroxyethylguanidine (creatinol) is a compound that has been known for several years in the pharmaceutical field where it found wide use as a tonic, an energetic agent, and a myotropic agent. The only method known to date for its preparation (Belgian Pat. No. 666,891) claims the action of quenched phosphorus oxychloride on the hydrobromide of N-methyl-N-hydroxyethylguanidine.

This method is certainly not satisfactory from the viewpoint of industrial use, because of both the known dangerousness implied in using phosphorus oxychloride in the presence of water, and the strong development of hydrochloric acid and hydrobromic acid occurring during the reaction and because of the difficulty in eliminating them.

In addition this is a reaction that runs over four days before it is completed. We have now found an extremely simple method for producing on an industrial basis and with high yields O-phosphate of N-methyl-N-hydroxyethylguanidine with high purity, this method eliminating, in particular, all inconveniences mentioned above.

Essentially the process of this invention consists in having the phosphate creatinol having the formula $$H_3PO_4 \cdot H_2N-\underset{\underset{NH}{\|}}{C}-\underset{CH_3}{N}-CH_2-CH_2OH$$

react with polyphosphoric acid.

Reagents are directly mixed, without diluent or solvent whatsoever being present, and brought to melting.

Heating of the molten mass is preferably time-extended under vacuum in order to eliminate the water as it forms and to accelerate the process.

The reaction on which the new process is based can schematically be represented as follows:

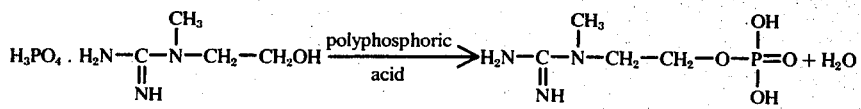

As shown, quite unexpectedly the creatinol salt changes into the corresponding ester with elimination of water.

The ester thus obtained is separated by precipitation with a proper organic solvent where the ester is practically insoluble while all reaction by-products and the residual starting product, if any, dissolve completely. Particularly appropriate solvents are ethanol and the cellosolves.

To obtain a very pure product having phosphorus content not exceeding 0.5% it is preferable to further purify the same dissolving the product precipitated with the organic solvent in water and then mixing the aqueous solution with an organic solvent that, besides possessing the characteristics above mentioned, can be mixed with water. The organic solvents mentioned above are also suitable for this purifying process.

The yield may reach as much as 90% of very pure product.

We now furnish hereinafter an illustrative example, that is, however, not limiting of the invention, it being well understood that any variation lying within the reach of the man skilled in the art is included in the scope of this invention.

EXAMPLE

In a reactor put 80 kg of polyphosphoric acid having the following composition: $H_5P_3O_{10}$ - 60%; $(HPO_3)_6$ - 10%; $H_4P_2O_7$ - 15%; $(HPO_3)_x$ - 10%; total content in $P_2O_5$ about 83%; this is heated to about 160° C.

Then 360 kg of creatinol phosphate are added to the polyphosphoric acid; continue to heat for about two hours under vacuum until the reaction water is eliminated.

The molten mass is then poured into ethanol at 95° C, the solution cooled down to 10° C and the precipitated product separated by centrifugation. The resulting product is dissolved in the minimum quantity of warm water and the solution poured into ethanol.

Thus 297 kg of the phosphoric ester of the creatinol are obtained having these characteristics:
m.p. 240° to 243° C
acidimetric titre within the range 97 to 103%
free phosphorus: lower than 0.5%
Fe content: lower than 50 ppm

I claim:

1. Process for preparing the phosphoric ester of N-methyl-N-hydroxyethylguanidine of the formula $$H_2N-\underset{\underset{NH}{\|}}{C}-\underset{CH_3}{N}-CH_2-CH_2-O-\underset{\underset{OH}{|}}{\overset{\overset{OH}{|}}{P}}=O$$

characterized in that the creatinol phosphate of the formula $$H_3PO_4 \cdot H_2N-\underset{\underset{NH}{\|}}{C}-\underset{CH_3}{N}-CH_2-CH_2-OH$$

is reacted with polyphosphoric acid in the molten state, under vacuum to eliminate the reaction water, and the obtained mass is poured into an organic solvent where the phosphoric ester of N-methyl-N-hydroxyethylguanidine is practically insoluble, whereas the rest of the reaction mixture is practically entirely soluble.

2. Process according to claim 1, wherein the phosphoric ester of N-methyl-N-hydroxyethylguanidine is purified by dissolving it in water and admixing the aqueous solution with a water miscible organic solvent where the phosphoric ester is practically insoluble.

3. Process according to claim 1, wherein the organic solvent is selected from the group consisting of ethanol and cellosolves.

4. Process according to claim 2, wherein the organic solvent is selected from the group consisting of ethanol and cellosolves.

* * * * *